United States Patent [19]

Tanaka

[11] Patent Number: 6,010,858

[45] Date of Patent: Jan. 4, 2000

[54] METHOD FOR EXPRESSION CLONING OF GENE ENCODING PROTEIN KINASE SUBSTRATE PROTEIN

[76] Inventor: Toshio Tanaka, 2673-2, Fujikata, Tsu-shi, Mie, Japan

[21] Appl. No.: 09/068,309

[22] PCT Filed: Nov. 5, 1996

[86] PCT No.: PCT/JP96/03234

§ 371 Date: May 7, 1998

§ 102(e) Date: May 7, 1998

[87] PCT Pub. No.: WO97/17439

PCT Pub. Date: May 15, 1997

[30] Foreign Application Priority Data

Nov. 7, 1995 [JP] Japan ................................ 7-288775

[51] Int. Cl.[7] ........................................... C12Q 1/68
[52] U.S. Cl. ................................... 435/6; 435/15
[58] Field of Search ............................. 435/6, 15

[56] References Cited

PUBLICATIONS

Carmel et al., *Analytical Biochemistry*, 1992, vol. 203, pp. 274–280.

*Primary Examiner*—James Ketter
*Attorney, Agent, or Firm*—Foley & Lardner

[57] ABSTRACT

The present invention provides a method for efficiently cloning DNA coding for a protein kinase substrate protein.

This method comprises plate-culturing a host into which DNA inserted into an expression vector has been introduced, transferring the expressed protein from the plate to a film by contacting the film onto the plate, removing the film from the plate, adding a labeled phosphate donor and protein kinase to the film to phosphorylate the protein, detecting the phosphoric acid label bonded to the protein, and isolating DNA from the clones on the plate corresponding to the sites on the film that exhibit a positive reaction.

21 Claims, No Drawings

METHOD FOR EXPRESSION CLONING OF GENE ENCODING PROTEIN KINASE SUBSTRATE PROTEIN

TECHNICAL FIELD

The present invention relates to an expression cloning method of a gene that codes for protein kinase substrate protein. According to the present invention, a gene can be efficiently cloned that codes for a protein which is a substrate of protein kinase having useful biological activity.

BACKGROUND ART

When cells are stimulated with a growth factor and so forth, information is transmitted inside the cells via receptors on the cell surface layer. In many cases, this transmission of information is known to be performed by phosphorylation of protein. Many receptors are protein kinases or form complexes with protein kinases. Information of growth factor etc. activates protein kinase in this manner resulting in phosphorylation of the target protein, which is then transmitted inside the cell so that the response of the cell begins.

Protein kinase is an enzyme that transfers the phosphoric acid at the γ-position of ATP to a hydroxyl group of serine, threonine, tyrosine and so forth, and plays the role of a central mechanism in the transmission of information into cells. Protein kinases play an important role in the function regulatory mechanisms of almost all cells. For example, they have been clearly shown to be involved in cell movement, cell growth, metabolic response, immune response and so forth. In this way, in order to understand the function regulatory mechanisms of cells, it is essential to determine the target proteins of protein kinases. However, since the substrate proteins of protein kinases are not always clear, many unknown aspects remain regarding their details.

Efforts have been made in the past to explain the phosphorylation reaction in which protein kinases are involved. For example, Carmel, G. & Kuret, J. reported that the substrate selectivity of protein kinase was analyzed by expressing a DNA library containing a mutant gene fragment of a protein kinase substrate protein constructed using the cassette mutation induction method in an *E. coli* expression system, and performing a phosphorylation reaction in the solid phase in the presence of protein kinase (Analytical Biochemistry (1992), 203, 274–280). However, this method is limited to analysis of the site that recognizes the substrate protein on the protein kinase, and there is no mention of expression cloning of a gene that codes for protein kinase substrate protein. Thus, a method for efficiently cloning a gene that codes for protein kinase substrate protein was unknown.

DISCLOSURE OF THE INVENTION

As a result of earnest studies conducted by the inventors of the present invention on a cloning method of a gene that codes for a protein kinase substrate protein, it was found that a protein coding for protein kinase substrate protein can be efficiently and easily acquired by expressing a DNA library containing various genes and directly identifying protein kinase substrate protein by using a phosphorylation reaction, thereby leading to completion of the present invention.

Thus, the present invention provides a method for cloning a gene that codes for protein kinase substrate protein at a high level of efficiency unattainable with conventional methods.

In order to solve the above-mentioned problems, the present invention provides an expression cloning method of a gene that codes for protein kinase substrate protein comprising: plate-culturing a host into which DNA containing an expression vector has been introduced, expressing said DNA, transferring protein produced by contacting a film onto said plate from said plate to said film, removing said film from said plate, adding a phosphate donor and protein kinase to said film to phosphorylate said protein, detecting phosphoric acid bonded to said protein, and isolating DNA from the host clones on the plate corresponding to the sites on the film that exhibit a positive reaction.

In the case said protein kinase substrate protein is a protein having phosphorylating ability on its own (a protein kinase substrate having a self-phosphorylating ability), it is not necessary to add protein kinase in the above-mentioned screening method.

Thus, the present invention also provides an expression cloning method of a gene that codes for protein kinase substrate protein having a self-phosphorylating ability comprising: plate-culturing a host into which DNA inserted into an expression vector has been introduced, expressing said DNA, transferring protein produced by contacting a film onto said plate from said plate to said film, removing said film from said plate, adding a phosphate donor to said film to phosphorylate said protein, detecting phosphoric acid bonded to said protein, and isolating DNA from the host clones on the plate corresponding to the sites on the film that exhibit a positive reaction.

Moreover, the present invention also provides an expression cloning method of a gene that codes for protein kinase substrate protein having a self-phosphorylating ability comprising: plate-culturing a host into which DNA inserted into an expression vector has been introduced, expressing said DNA, transferring protein produced by contacting a film onto said plate from said plate to said film, removing said film from said plate, adding a phosphate donor to said film to phosphorylate said protein, immunologically detecting phosphoric acid bonded to said protein, and isolating DNA from the host clones on the plate corresponding to the sites on the film that exhibit a positive reaction.

According to the present invention, it is easy to obtain new substrate proteins of various protein kinases from numerous cells and tissues, thereby making it possible to screen pharmaceuticals that have these substrate proteins as their target molecules.

BEST MODE FOR CARRYING OUT THE INVENTION

In carrying out the present invention, the first step is to prepare a DNA library that is constructed by inserting DNA into an expression vector. Any cells and tissues from which DNA that codes for the target protein kinase substrate protein to be cloned can be used for the DNA acquisition source, examples of which include tissues such as brain, thyroid, lung, heart, thymus, pancreas, spleen, kidney, adrenal, intestine, skeletal muscle, bone marrow, epithelium, placenta, blood vessel and blood, as well as cells originating in these tissues. Although cDNA or genomic DNA acquired from these cells and tissues is suitable, cDNA is preferable. In the case of cDNA, mRNA can be purified from the target cells or tissue after which cDNA can be synthesized by reverse transcriptase and used as DNA. The above-mentioned cells or tissue may be normal, or in the case of targeting protein kinase substrate protein involved in a specific disease, the cells or tissue may be that in the corresponding disease state or cells and tissue can be used originating in an artificially produced disease state, namely in various types of disease models. In addition, these cells and tissues may come from fetuses or adults, and from humans or animals other than humans.

Preparation of a DNA library can be performed in accordance with known routine methods. Any vectors routinely used in the preparation of DNA libraries can be used for the expression vectors for preparing the DNA library, examples of which include phage vectors and plasmid vectors. These can contain routine, known expression control sequences such as promoters and enhancers, and are able to express the DNA contained therein. Moreover, it is preferable that they contain an expression induction sequence. Examples of phage vectors include λZAP and λgt11.

The host that forms a DNA library should be a host normally used in DNA libraries, that exhibits vector susceptibility. Moreover, it is preferable that the host allows control of induction of expression. The expression vector is preferably that which expresses the inserted DNA in the presence of an expression inducer, and examples of expression induction sequences for this purpose include the lac promoter of the lac operon and tac promoter modified from the lac promoter. In addition, isopropyl-β-D-thiogalactoside (IPTG) is used as an expression inducer corresponding to said promoter.

In carrying out the method of the present invention, host cells transformed by an expression vector containing DNA, that composes the above-mentioned DNA library, are first inoculated onto a solid plate medium and cultured. Culturing should be performed under normal known conditions so that the DNA library in the host cells is suitably expressed. As a result, in the case of using, for example, a phage vector for the expression vector, a plaque is formed. As a result of this culturing, in the case of an expression vector that does not require induction of expression, protein is produced in the plaque portion by expression of the inserted DNA and by contacting a film onto the above-mentioned plate, the protein that is produced is transferred to the film. In the case where the expression vector requires an expression inducer for expression of DNA, an expression inducer is added. When adding an expression inducer, the expression inducer is either added directly to the culture liquid in advance, or an expression inducer is impregnated into the film. After adding the expression inducer, said film is brought into contact with the surface of the above-mentioned plate. As a result, the expression inducer is transferred from the film to the plate medium, production of protein coded for by said DNA is induced, and that protein moves into the above-mentioned film.

The film used in the present invention is preferably a film that can be impregnated with expression inducer and allows the transfer of protein, and normally used plotting films such as nitrocellulose film or Nylon film are preferable.

Next, the film may be washed to remove medium ingredients, cells and so forth that have transferred from the plate, and then treated with a protein denaturation agent. Examples of protein denaturation agents that can be used include guanidine hydrochloride, urea or various types of reducing reagents. Protein denaturation is performed by treating the above-mentioned film with a buffer containing the above-mentioned denaturation agent such as Tris-HCl buffer. This denaturation is performed to ensure that the phosphorylation reaction by protein kinase occurs efficiently.

Next, by washing the film with a washing liquid such as Tris-HCl buffer, the above-mentioned protein denaturation agent is washed away. Next, the protein on the film is regenerated by treating the film with a regenerating agent.

Next, after washing the film and removing the regenerating agent, a solution containing phosphate donor and protein kinase is applied to the film. However, in the case where the protein kinase substrate protein has a self-phosphorylating ability, it is not necessary to add protein kinase. Consequently, if a host clone (positive clone) that contains DNA which codes for protein kinase substrate protein is present on the above-mentioned plate, the corresponding protein on the film will be phosphorylated by phosphoric acid from the phosphate donor due to the action of protein kinase, and by detecting this phosphoric acid, the locations of positive clones on the plate can be determined. Furthermore, ATP (adenosine triphosphate) is preferable for the phosphate donor.

With respect to the method of detecting phosphoric acid, the phosphoric acid contained in the phosphate donor is labeled with a radioactive substance, and protein kinase substrate protein to which the phosphoric acid is bonded can be detected according to the radioactivity of said labeled phosphoric acid. Radioisotopes of phosphorous are normally used for the label. More specifically, $\gamma^{32}$P-ATP, in which the phosphorous of phosphoric acid at the $\gamma$ position is substituted with $^{32}$P, can be used for the labeled phosphate donor. Host clones on the above-mentioned plate at the corresponding positions can be identified by identifying positive spots by autoradiography. Examples of protein kinase that can be used in the present invention include cAMP-dependent protein kinase, cGMP-dependent protein kinase, protein kinase C, calmodulin-dependent protein kinase, phosphorylase kinase, myosin light-chain kinase, casein kinase, MAP (mitogen-activated protein) kinase and double-chain RNA-dependent kinase. In addition, examples of protein kinase substrate protein having a self-phosphorylation ability include nucleoside diphosphate kinase.

Further, in addition to using radioactive-labeled phosphoric acid, phosphoric acid bonded to protein kinase substrate protein may also be detected immunologically.

Host clones obtained in this manner can be purified by repeatedly reacting in later steps from the above-mentioned plate culture. Once a positive clone is identified in this manner, the vector is isolated from the host clone cells in accordance with routine methods, and the target DNA can be cleaved from the vector.

INDUSTRIAL APPLICABILITY

According to the method of the present invention, DNA coding for protein kinase substrate protein can be cloned extremely efficiently and easily from various types of normal and pathological cells and tissues, thereby enabling the screening of pharmaceuticals that have these substrate proteins for their target molecules.

EXAMPLES

Although the following provides a detailed explanation of the present invention through the Examples, the present invention is not limited to the Examples indicated below.

Example 1

Uni-ZAPXR library (Stratagene) was used for the rat brain expression cDNA library. *E. coli* (XL1-Blue, Stratagene) was infected with the cDNA library, mixed with top agarose and inoculated onto a square plate measuring 12 cm on a side at the rate of about $1\times10^4$ pfu.

The plate was incubated for about 3 to 4 hours at 42° C. After the plaque had reached a certain size, a nitrocellulose film impregnated with 20 mM isopropyl-β-D-thiogalactoside (IPTG) was placed on the plate followed by incubation at 37° C. for about 3 hours to produce protein and transfer it onto the film. After marking the film and the plate, the nitrocellulose film was removed, immersed in solution A (50 mM Tris-HCl (pH 7.4), 0.2 M NaCl, 0.1% Triton X-100, 0.4% Ficoll) and allowed to stand overnight. The nitrocellulose film was then washed thoroughly with solution B (10 mM Tris-HCl (pH 7.4), 0.15 M NaCl, 1 mM EGTA, 0.1% Triton X-100 and 5 MM $MgCl_2$).

The washed nitrocellulose film was placed in a Petri dish followed by the addition of solution C (10 mM Hepes (pH 7.5), 5 mM $MgCl_2$, 1 mM EGTA, 0.32 μg/ml catalytic subunit of cAMP-dependent protein kinase, 10 μM [$\gamma^{32}P$] ATP) to start the reaction. The nitrocellulose film was then incubated for 10 minutes at room temperature. The reaction was stopped with solution D (50 mM $Na_4P_2O_7$, 0.2 M NaCl, 10 mM EDTA, 0.1% Triton X-100). After washing several times with solution D, the nitrocellulose film was dried followed by autoradiography. A single clone was obtained by repeating screening 2 to 3 times on the resulting positive plaque, after which the nucleotide sequence of that clone was determined. As a result, it was clearly shown that the clone contained a portion of rat brain HEM2 in the insert. It was clear that the substrate confirmation sequences of cAMP-dependent protein kinase (R-X-X-S and R-X-S) were contained in the amino acid sequence of that portion.

Example 2

Cloning of a Gene Coding for Protein Kinase Substrate Protein Having Autokinase Activity Restriction enzymes (Takara, Nippon Gene and Bio Labs), nam-DNA ligase (Promega), Taq DNA polymerase and ribonuclease A (Takara) were used according to the instructions of the manufacturers. A nitrocellulose filter (Schleicher & Schell) was used for solid-phase phosphorylation screening assay. Uni-ZAP (trade name) XR phage library was acquired from Stratagene, and plasmid vector pET3 was purchased from Novergen.

XL-1 Blue was grown to the late logurithmic phase in a LB medium of pH 7.5 containing 0.1% maltose. The cells were then infected with a suitable amount of a phage library for 20 minutes at 37° C. in 0.1 ml of 10 mM $MgSO_4$. The infected cells were diluted with 8 ml of LB medium containing 0.7% melted agarose, and the suspension was carefully poured into an LB plate. After allowing the poured agarose to dry completely at room temperature, the plate was incubated for 3 to 4 hours at 42° C. A nitrocellulose filter pre-saturated with 20 mM isopropyl-β-D-thiogalactopyranoside (IPTG) for 15 minutes at 37° C. was sequentially layered onto the plate. Next, the plate was incubated for 2 to 8 hours at 37° C. After the cell plaque had suitably grown and the filter was marked with a needle, the plate was allowed to stand for several minutes at 4° C. After removing the filter, the plate was washed twice for 15 minutes at 4° C. in TBST buffer (10 mM Tris-HCl (pH 8.0), 0.15 M NaCl, 0.05% (v/v) Tween20), and then incubated from one hour to overnight at 4° C. in a blocking buffer (50 mM Tris-HCl (pH 7.5), 0.2 M NaCl, 0.4% Ficoll 400, 0.1% (v/v) Triton X-100).

The plaque filter prepared in this manner was washed three times for 15 minutes each in a washing buffer (10 mM Tris-HCl (pH 7.5), 0.15 M NaCl, 0.1% Triton X-100, 5 mM $MgCl_2$), and incubated for 10 minutes at 20° C. with 20 mM [$\gamma$-$^{32}P$]ATP in a phosphorylation mixture (10 mM HEPES (pH 7.5), 10 mM $MgCl_2$, 1 mM EGTA). Finally, the filter was washed for 30 minutes in a stopping buffer (50 mM $Na_2PO_4$, 0.2 M NaCl, 10 mM EDTA, 0.1% Triton X-100), floated twice for 5 minutes each in 10 mM HCl, and again washed in a stopping buffer. After allowing to dry, the filter was then subjected to autoradiography. After exposing for 12 to 36 hours at −70° C., a favorable signal was obtained.

After purifying the plaque, a pBlaescript phagemid containing an insert of the positive clone was cut out according to the instructions of the manufacturer and its sequence was determined. When this sequence was expressed, a protein kinase substrate protein having a self-phosphorylating ability was obtained.

I claim:

1. An expression cloning method of a gene coding for a protein kinase substrate protein comprising the steps of:

plate-culturing a host into which DNA inserted into an expression vector has been introduced wherein said DNA has been cloned from a cell or tissue without mutagenesis, expressing said DNA, transferring protein produced by contacting a film onto said plate from said plate to said film, removing said film from said plate, adding a phosphate donor and protein kinase to said film to phosphorylate said protein, detecting phosphoric acid bonded to said protein, and isolating DNA from the host clones on the plate corresponding to the sites on the film that exhibit a positive reaction.

2. An expression cloning method according to claim 1 wherein said phosphate donor is ATP.

3. An expression cloning method according to claim 1 wherein phosphoric acid contained in said phosphate donor is labeled with a radioactive substance, and protein kinase substrate protein to which phosphoric acid is bonded is detected by the radioactivity of said radioactively labeled phosphoric acid.

4. An expression cloning method according to claim 3 wherein said protein kinase is a cAMP-dependent protein kinase, and said labeled phosphate donor is $\gamma^{32}P$-ATP.

5. An expression cloning method of a gene coding for a protein kinase substrate protein comprising the steps of:

plate-culturing a host into which DNA inserted into an expression vector has been introduced, expressing said DNA, transferring protein produced by contacting a film onto said plate from said plate to said film, removing said film from said plate, adding a phosphate donor and protein kinase to said film to phosphorylate said protein, immunologically detecting phosphoric acid bonded to said protein, and isolating DNA from the host clones on the plate corresponding to the sites on the film that exhibit a positive reaction.

6. An expression cloning method according to claim 1 wherein said DNA is cDNA.

7. An expression cloning method according to claim 1 wherein said expression vector is able to express inserted DNA only in the presence of an expression inducer, and said DNA is expressed by addition of said expression inducer.

8. An expression cloning method according to claim 1 wherein the method for said detection is autoradiography.

9. An expression cloning method of a gene coding for a protein kinase substrate protein having a self-phosphorylating ability comprising the steps of:

plate-culturing a host into which DNA inserted into an expression vector has been introduced wherein said DNA has been cloned from a cell or tissue without mutagenesis, expressing said DNA, transferring protein produced by contacting a film onto said plate from said plate to said film, removing said film from said plate, adding a phosphate donor to said film to phosphorylate said protein, detecting phosphoric acid bonded to said protein, and isolating DNA from the host clones on the plate corresponding to the sites on the film that exhibit a positive reaction.

10. An expression cloning method according to claim 9 wherein said phosphate donor is ATP.

11. An expression cloning method according to claim 9 wherein phosphoric acid contained in said phosphate donor is labeled with a radioactive substance, and protein kinase substrate protein to which phosphoric acid is bonded is detected by the radioactivity of said radioactively labeled phosphoric acid.

12. An expression cloning method according to claim 11 wherein said substrate protein is nucleoside diphosphate kinase.

13. An expression cloning method of a gene coding for a protein kinase substrate protein having a self-phosphorylating ability comprising the steps of:

plate-culturing a host into which DNA inserted into an expression vector has been introduced, expressing said DNA, transferring protein produced by contacting a film onto said plate from said plate to said film, removing said film from said plate, adding a phosphate donor to said film to phosphorylate said protein, immunologically detecting phosphoric acid bonded to said protein, and isolating DNA from the host clones on the plate corresponding to the sites on the film that exhibit a positive reaction.

14. An expression cloning method according to claim 9 wherein said DNA is cDNA.

15. An expression cloning method according to claim 9 wherein said expression vector is able to express inserted DNA only in the presence of an expression inducer, and said DNA is expressed by addition of said expression inducer.

16. An expression cloning method according to claim 9 wherein the method of said detection is autoradiography.

17. An expression cloning method according to claim 5, wherein said DNA is cDNA.

18. An expression cloning method according to claim 5, wherein said expression vector is able to express inserted DNA only in the presence of an expression inducer, and said DNA is expressed by addition of said expression inducer.

19. An expression cloning method according to claim 13, wherein said DNA is cDNA.

20. An expression cloning method according to claim 13, wherein said expression vector is able to express inserted DNA only in the presence of an expression inducer, and said DNA is expressed by addition of said expression inducer.

21. An expression cloning method according to claim 13, wherein the method of said detection is autoradiography.

* * * * *